(12) United States Patent
Wolber et al.

(10) Patent No.: US 7,588,889 B2
(45) Date of Patent: *Sep. 15, 2009

(54) CHEMICAL ARRAYS AND METHODS OF USING THE SAME

(75) Inventors: Paul K. Wolber, Los Altos, CA (US); Robert H. Kincaid, Half Moon Bay, CA (US); Douglas Amorese, Los Altos, CA (US); Diane Ilsley-Tyree, San Jose, CA (US); Andrew S. Atwell, Campbell, CA (US); Mel N. Kronick, Palo Alto, CA (US); Eric M. Leproust, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 741 days.

This patent is subject to a terminal disclaimer.

(21) Appl. No.: 11/008,603

(22) Filed: Dec. 8, 2004

(65) Prior Publication Data

US 2005/0148004 A1 Jul. 7, 2005

Related U.S. Application Data

(63) Continuation-in-part of application No. 09/628,472, filed on Jul. 31, 2000.

(51) Int. Cl.
*C12Q 1/68* (2006.01)
*C12M 1/00* (2006.01)
*C07H 21/04* (2006.01)

(52) U.S. Cl. .................... 435/6; 435/283.1; 435/287.2; 536/23.1; 536/25.3

(58) Field of Classification Search ........................ None
See application file for complete search history.

(56) References Cited

U.S. PATENT DOCUMENTS

| | | | |
|---|---|---|---|
| 4,734,363 A | 3/1988 | Dattagupta et al. | |
| 5,215,899 A | 6/1993 | Dattagupta | |
| 5,405,746 A | 4/1995 | Uhlen | |
| 5,436,327 A | 7/1995 | Southern et al. | |
| 5,472,672 A | 12/1995 | Brennan | |
| 5,529,756 A | 6/1996 | Brennan | |
| 5,652,099 A | 7/1997 | Conrad | |
| 5,795,714 A | 8/1998 | Cantor et al. | |
| 5,814,700 A | 9/1998 | Brennan | |
| 5,837,858 A | 11/1998 | Brennan | |
| 6,013,440 A * | 1/2000 | Lipshutz et al. | 435/6 |
| 6,235,483 B1 | 5/2001 | Wolber et al. | |
| 6,280,950 B1 | 8/2001 | Lipshutz et al. | |
| 6,307,039 B1 | 10/2001 | Southern et al. | |
| 6,692,915 B1 * | 2/2004 | Nallur | 435/6 |

FOREIGN PATENT DOCUMENTS

| | | |
|---|---|---|
| EP | 1180548 | 2/2002 |
| WO | WO 93/17126 | 9/1993 |
| WO | WO 99/07888 | 2/1999 |
| WO | WO 00/65095 | 11/2002 |

OTHER PUBLICATIONS

Leproust et al. "Charaterization of Oligodeoxyribonucleotide Synthesis on Glass Plates," (2001) Nucleic Acids Research, 29(10):2171-2180.

* cited by examiner

*Primary Examiner*—B J Forman

(57) ABSTRACT

Methods and compositions for generating mixtures of product molecules from an initial chemical array are provided. In the subject methods, a chemical array of surface immobilized first moieties is subjected to cleavage conditions such that a composition of solution phase first moieties is produced. The resultant composition of solution phase first moieties is then contacted with one or more reactants to produce a mixture of product molecules that are different from the first moieties. Also provided are the arrays employed in the subject methods and kits for practicing the subject methods.

9 Claims, No Drawings

CHEMICAL ARRAYS AND METHODS OF USING THE SAME

CROSS-REFERENCE TO RELATED APPLICATIONS

The present application is a continuation-in-part of application Ser. No. 09/628,472 filed on Jul. 31, 2000; the disclosure of which is herein incorporated by reference.

INTRODUCTION

Chemical arrays, such as nucleic acid and protein arrays, are finding increasing use in a variety of different applications, and in doing so are making a significant impact in a variety of different fields, including research, medicine, and the like. In many instances, arrays include regions of usually different composition arranged in a predetermined configuration on a substrate. These regions (sometimes referenced as "features") are positioned at known respective locations ("addresses") on the substrate and are therefore "addressable."

In using such arrays, the arrays are, in many applications, exposed to a sample. Upon sample exposure, the arrays will exhibit an observed binding pattern that is dependent on the sample composition to which they have been contacted. This observed binding pattern is then detected upon interrogating the array. In the example of a nucleic acid array, the observed binding pattern is then employed to determine the presence and/or concentration of one or more polynucleotide components of the sample. Representative methods for sample preparation, labeling, and hybridizing include those disclosed in U.S. Pat. Nos. 6,201,112; 6,132,997; and 6,235,483; as well as published United States patent application 20020192650.

Arrays can be fabricated by depositing previously obtained biopolymers onto a substrate, or by in situ synthesis methods. The in situ fabrication methods include those described in U.S. Pat. Nos. 5,449,754 and 6,180,351 as well as published PCT application no. WO 98/41531 and the references cited therein. Further details of fabricating biopolymer arrays are described in U.S. Pat. Nos. 6,242,266; 6,232,072; 6,180,351 and 6,171,797. Other techniques for fabricating biopolymer arrays include known light directed synthesis techniques.

As the technology of making and using arrays continues to advance, there is a continued interest in the development of new applications for these powerful tools.

SUMMARY OF THE INVENTION

Methods and compositions for generating mixtures of product molecules from an initial chemical array are provided. In the subject methods, a chemical array of surface immobilized first moieties is subjected to cleavage conditions such that a composition of solution phase first moieties is produced. The resultant composition of solution phase first moieties is then contacted with one or more reactants to produce a mixture of product molecules that are different from the first moieties. Also provided are the arrays employed in the subject methods and kits for practicing the subject methods.

Aspects of the invention include: (a) subjecting an array of a plurality of features each including first moieties immobilized on a surface of a solid support via a cleavable domain having a cleavable region to conditions sufficient to cleave the cleavable linker and generate a solution phase composition of said first moieties; and (b) contacting the resultant solution phase composition of first moieties with one or more reactants to produce a mixture of product molecules that are different from the first moieties. In certain embodiments, the first moieties are polymers, e.g., biopolymers, such as nucleic acids or polypeptides. In certain embodiments, the cleavable region of the cleavable domain is chemically cleavable, e.g., it is a base or acid labile linker, while in other embodiments it is enzymatically cleavable. In certain embodiments, the one or more reactants comprises an enzymatic activity, as is found in an enzymatic reaction system, such as a template dependent polymerase reaction system. In certain embodiments, the product molecules are nucleic acids, such as deoxyribonucleic acids or ribonucleic acids.

Also provided are arrays that include a plurality of nucleic acid features each including nucleic acids immobilized on a surface of substrate via a cleavable linker. In representative embodiments, the surface immobilized single-stranded nucleic acids are described by the formula:

surface-L-V- wherein:

L is a cleavable domain having a cleavable region; and

V is a variable domain;

where the single-stranded nucleic acid may be oriented with its 3' or 5' end proximal to the substrate surface and the variable domain V of the surface immobilized single-stranded nucleic acids differs between features.

Also provided are kits that include: (a) an as described above; and (b) a cleavage agent for cleaving the cleavable linker. In certain embodiments, the kits further include one or more members of an enzymatic reaction system, as reviewed above.

DEFINITIONS

A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. As such, this term includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "mRNA" means messenger RNA.

A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides.

An "oligonucleotide" generally refers to a nucleotide multimer of about 10 to 100 nucleotides in length, while a "polynucleotide" includes a nucleotide multimer having any number of nucleotides.

A chemical "array", unless a contrary intention appears, includes any one, two or three-dimensional arrangement of addressable regions bearing a particular chemical moiety or moieties (for example, biopolymers such as polynucleotide sequences) associated with that region. For example, each region may extend into a third dimension in the case where the substrate is porous while not having any substantial third dimension measurement (thickness) in the case where the substrate is non-porous. An array is "addressable" in that it has multiple regions (sometimes referenced as "features" or "spots" of the array) of different moieties (for example, different polynucleotide sequences) such that a region at a particular predetermined location (an "address") on the array will detect a particular target or class of targets (although a feature may incidentally detect non-targets of that feature). The target for which each feature is specific is, in representative embodiments, known. An array feature is generally homogenous in composition and concentration and the features may be separated by intervening spaces (although arrays without such separation can be fabricated).

In the case of an array, the "target" will be referenced as a moiety in a mobile phase (typically fluid), to be detected by probes ("target probes") which are bound to the substrate at the various regions. However, either of the "target" or "target probes" may be the one which is to be detected by the other (thus, either one could be an unknown mixture of polynucleotides to be detected by binding with the other). "Addressable set of probes" and analogous terms refers to the multiple regions of different moieties supported by or intended to be supported by the array surface.

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

"Hybridizing" and "binding", with respect to polynucleotides, are used interchangeably.

A "plastic" is any synthetic organic polymer of high molecular weight (for example at least 1,000 grams/mole, or even at least 10,000 or 100,000 grams/mole.

"Flexible" with reference to a substrate or substrate web (including a housing or one or more housing component such as a housing base and/or cover), references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C. "Rigid" refers to a substrate (including a housing or one or more housing component such as a housing base and/or cover) which is not flexible, and is constructed such that a segment about 2.5 by 7.5 cm retains its shape and cannot be bent along any direction more than 60 degrees (and often not more than 40, 20, 10, or 5 degrees) without breaking.

When one item is indicated as being "remote" from another, this descriptor indicates that the two items are at least in different buildings, and may be at least one mile, ten miles, or at least one hundred miles apart. When different items are indicated as being "local" to each other they are not remote from one another (for example, they can be in the same building or the same room of a building). "Communicating", "transmitting" and the like, of information reference conveying data representing information as electrical or optical signals over a suitable communication channel (for example, a private or public network, wired, optical fiber, wireless radio or satellite, or otherwise). Any communication or transmission can be between devices which are local or remote from one another. "Forwarding" an item refers to any means of getting that item from one location to the next, whether by physically transporting that item or using other known methods (where that is possible) and includes, at least in the case of data, physically transporting a medium carrying the data or communicating the data over a communication channel (including electrical, optical, or wireless). "Receiving" something means it is obtained by any possible means, such as delivery of a physical item (for example, an array or array carrying package). When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication it is received as a result of a transmission of that information from elsewhere (local or remote).

When two items are "associated" with one another they are provided in such a way that it is apparent one is related to the other such as where one references the other. For example, an array identifier can be associated with an array by being on the array assembly (such as on the substrate or a housing) that carries the array or on or in a package or kit carrying the array assembly. Items of data are "linked" to one another in a memory when a same data input (for example, filename or directory name or search term) retrieves those items (in a same file or not) or an input of one or more of the linked items retrieves one or more of the others. In particular, when an array layout is "linked" with an identifier for that array, then an input of the identifier into a processor which accesses a memory carrying the linked array layout retrieves the array layout for that array.

A "computer", "processor" or "processing unit" are used interchangeably and each references any hardware or hardware/software combination which can control components as required to execute recited steps. For example a computer, processor, or processor unit includes a general purpose digital microprocessor suitably programmed to perform all of the steps required of it, or any hardware or hardware/software combination which will perform those or equivalent steps. Programming may be accomplished, for example, from a computer readable medium carrying necessary program code (such as a portable storage medium) or by communication from a remote location (such as through a communication channel).

A "memory" or "memory unit" refers to any device which can store information for retrieval as signals by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

An array "assembly" includes a substrate and at least one chemical array on a surface thereof. Array assemblies may include one or more chemical arrays present on a surface of a device that includes a pedestal supporting a plurality of prongs, e.g., one or more chemical arrays present on a surface of one or more prongs of such a device. An assembly may include other features (such as a housing with a chamber from which the substrate sections can be removed). "Array unit" may be used interchangeably with "array assembly".

"Reading" signal data from an array refers to the detection of the signal data (such as by a detector) from the array. This data may be saved in a memory (whether for relatively short or longer terms).

A "package" is one or more items (such as an array assembly optionally with other items) all held together (such as by a common wrapping or protective cover or binding). Normally the common wrapping will also be a protective cover (such as a common wrapping or box) which will provide additional protection to items contained in the package from exposure to the external environment. In the case of just a single array assembly a package may be that array assembly with some protective covering over the array assembly (which protective cover may or may not be an additional part of the array unit itself).

It will also be appreciated that throughout the present application, that words such as "cover", "base" "front", "back", "top", "upper", and "lower" are used in a relative sense only.

"May" refers to optionally.

When two or more items (for example, elements or processes) are referenced by an alternative "or", this indicates that either could be present separately or any combination of them could be present together except where the presence of one necessarily excludes the other or others.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO4, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions that determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2'SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

As such, the term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch, wherein the total number of mismatched nucleotides is no more than about 3 for a sequence about 15 to about 35 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. Computer software for calculating duplex stability is commercially available from a variety of vendors.

Stringent, sequence-specific hybridization conditions, under which an oligonucleotide will hybridize only to the exactly complementary target sequence, are well known in the art (see, e.g., Sambrook et al., 2001, Molecular Cloning—A Laboratory Manual, Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions allows sequence mismatches to be tolerated; the degree of mismatch tolerated can be controlled by suitable adjustment of the hybridization conditions.

DESCRIPTION OF THE SPECIFIC EMBODIMENTS

Methods and compositions for generating mixtures of product molecules from an initial chemical array are provided. In the subject methods, a chemical array of surface immobilized first moieties is subjected to cleavage conditions such that a composition of solution phase first moieties is produced. The resultant composition of solution phase first moieties is then contacted with one or more reactants to produce a mixture of product molecules that are different from the first moieties. Also provided are the arrays employed in the subject methods and kits for practicing the subject methods.

Before the present invention is further described, it is to be understood that this invention is not limited to the particular embodiments described herein, as such may, of course, vary. It is also to be understood that the terminology used herein is for the purpose of describing particular representative embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. The figures shown herein are not necessarily drawn to scale, with some components and features being exaggerated for clarity.

As summarized above, the subject invention provides array-based methods for generating or producing pluralities of distinct product molecules from an initial population of first moieties. By plurality is meant at least 2, such as at least 5, including at least 10, where the number of distinct product molecules in the plurality may be at least about 25, at least about 50, at least about 100, at least about 500, at least about 1000 or more, such as at least about 5,000, at least about 10,000, at least about 25,000 or more.

The subject methods of producing the above-described pluralities are array-based methods, where a feature of the subject methods is that a chemical array is employed as a source of first moieties from which the product molecules are produced via a chemical reaction that employs on or more reactants, as described in greater detail below. The term chemical array is, as described above, a composition of matter that includes a plurality of distinct feature of chemical moieties, referred to herein conveniently as first moieties. In representative embodiments, the chemical moieties are biopolymers, e.g., polypeptides or nucleic acids. In representative embodiments, the nucleic acids are, as described above, ribonucleic acids or deoxyribonucleic acids. The particular nature of the chemical moieties of the array employed in the subject methods necessarily depends on the nature of the product composition to be produced. For example, when the product composition is a nucleic acid composition, the chemical array employed is, in many embodiments, a nucleic acid array. Alternatively, when the product composition is a polypeptide composition, the chemical array employed is, in many embodiments, a polypeptide array.

In practicing the subject methods, the first step of representative embodiments is to subject a chemical array of first moieties to cleavage conditions sufficient to cleave or separate the surface immobilized first moieties of the features of the array from the solid support to produce a product composition of solution phase first moieties, e.g., by action of a restriction endonuclease, by action of a chemical cleavage agent, as elaborated further below. The resultant composition of solution phase first moieties is then contacted with one or more reactants in a reaction step to produce a composition of product molecules. Each of these steps of this representative embodiment is now described separately in greater detail.

The initial array employed in the first step of the subject methods, which may conveniently be referred to as the solution phase first moiety generation step, is (in representative embodiments) a substrate having a planar surface on which is immobilized a plurality of distinct chemical features of surface immobilized first moieties. As indicated above, the surface immobilized first moieties may be a variety of different types of compounds, but in representative embodiments are biopolymeric compounds, such as polypeptides and nucleic acids. Accordingly, for ease of convenience in further describing the invention, the invention will be described in terms of the representative nucleic acid embodiments. However, in certain embodiments, the biopolymeric compounds are not nucleic acids, but instead non-nucleic acid biopolymers, e.g., polypeptides.

The surface immobilized nucleic acids of a given feature on the array are made up of single-stranded nucleic acids, and in representative embodiments single stranded deoxyribonucleic acids (where a single-stranded nucleic acid is a nucleic acid that is not hybridized to a second, non-covalently bound nucleic acid). The surface immobilized single-stranded nucleic acids are characterized by including: (a) a variable domain; and (b) a cleavable domain, where the cleavable domain includes a region (e.g., site or sequence) that is cleavable, e.g., such that the cleavable domain serves as a cleavable linker; where the variable domain is separated from the array surface by the cleavable domain. The cleavable domain may or may not be a constant domain, as desired. As such, in certain embodiments, the cleavable domain will be the same or identical for all of the surface-immobilized compounds of the array, while in other embodiments the various surface displayed compounds, or sets thereof, may have differing cleavable domains.

The initial arrays employed in the subject methods may be generated de novo or obtained as a pre-made array from a commercial source, where in either case the array will have the characteristics described below. Arrays of nucleic acids are known in the art, where representative arrays that may be modified to become arrays of the subject invention as described below, include those described in: U.S. Pat. Nos. 6,656,740; 6,613,893; 6,599,693; 6,589,739; 6,587,579; 6,420,180; 6,387,636; 6,309,875; 6,232,072; 6,221,653; and 6,180,351 and the references cited therein.

The number of nucleic acid features of the initial or precursor array may vary, where the number of features present on the surface of the array may be at least 2, 5, or 10 or more such as at least 20 and including at least 50, where the number may be as high as about 100, as about 500, as about 1000, as about 5000, as about 10000 or higher. In representative embodiments, the subject arrays have a density ranging from about 100 to about 100,000 features/cm$^2$, such as from about 500 to about 20,000 features/cm$^2$, including from about 1000 to about 20,000 features/cm$^2$. In representative embodiments, the density of single-stranded nucleic acids within a given feature is selected to optimize efficiency of the RNA polymerase. In certain of these representative embodiments, the density of the single-stranded nucleic acids may range from about $10^{-3}$ to about 1 pmol/mm$^2$, such as from about $10^{-2}$ to about 0.1 pmol/mm$^2$, including from about $5 \times 10^{-2}$ to about 0.1 pmol/mm$^2$.

As mentioned above, each distinct surface immobilized nucleic acid of the features on the array includes a variable domain separated from the surface of the solid support by a cleavable domain having a cleavable site, e.g., residue, sequence, etc. The variable domains of the features of the precursor array have sequences that are chosen based on the particular application in which the array is to be used, and specifically the intended use of the product solution phase mixture of first moieties produced using the array in accordance with the subject methods. The length of the variable domain may vary considerably and will be chosen based on the intended use of the solution phase first moieties, and in representative embodiments, ranges from about 10 to about 150 nt, such as from about 15 to about 100 nt and including from about 20 to about 80 nt.

As mentioned above, in addition to the variable domain, each surface immobilized nucleic acid present on the array includes a cleavable domain having a cleavable region. The cleavable region of the cleavable domain may be cleavable by a number of different mechanisms. In certain embodiments, the cleavable domain includes a sequence of residues that, when present in duplex format, is recognized and cleaved by a restriction endonuclease. A large number of restriction endonucleases are known to those of skill in the art. Specific restriction endonuclease recognized sites of interest that may make up the subject recognition sequence include, but are not limited to: Hinc II and the like. The length of the endonuclease recognition domain in these embodiments may range from about 4 nucleotides to about 8 nucleotides, such as from about 5 nucleotides to about 6 nucleotides. In yet other embodiments, the cleavable domain, and particularly the cleavable region thereof, may be cleaved by light, i.e. photocleavable, or the domain may be chemically cleavable, e.g., acid or base labile. In such domains, the domain will comprise a cleavable moiety that is either photo or chemically cleavable. Photocleavable or photolabile moieties that may be incorporated into the constant domain may include, but are not limited to: o-nitroarylmethine and arylaroylmethine, as well as derivatives thereof, and the like. Chemically cleavable moieties that may be incorporated into the constant domain may include, but are not limited to: dialkoxysilane, β-cyano ether, amino carbamate, dithoacetal, disulfide, and the like.

In representative embodiments, each surface immobilized nucleic acid on the array employed in the subject methods is described by the following formula:

surface-L-V- wherein:
L is a cleavable domain having a cleavable region; and
V is said surface distal variable domain;
where each of the above features is as described above In certain of these representative embodiments, only the variable domain V of said surface immobilized single-stranded nucleic acids differs between features. As indicated above, the single-stranded nucleic acid may be oriented such that either the 3' or 5' end of the molecule is proximal to the substrate surface.

The subject arrays are provided by any convenient means, including obtaining them from a commercial source or by synthesizing them de novo. To synthesize the arrays employed in the subject methods, the first step is generally to determine the nature of the mixture of nucleic acids that is to be produced using the subject array according to the subject methods. For example, where the solution phase moieties are to be employed as template directing the synthesis of product nucleic acids, the variable domains of the surface immobilized nucleic acids are chosen based on the sequences of the desired product nucleic acids. Any convenient method may be employed to determine the sequences of the surface immobilized nucleic acids, including probe design algorithms, including but not limited to those algorithms described in U.S. Pat. No. 6,251,588 and published U.S. Application Nos. 20040101846; 20040101845; 20040086880; 20040009484; 20040002070; 20030162183 and 20030054346; the disclosures of which are herein incorporated by reference. Following identification of the probe sequences as defined above, an array is produced in which each of the probe sequences of the identified or designed set of sequences is present.

Following provision of the array employed in the subject methods, as described above, the next step is to cleave the surface immobilized nucleic acids of the array features from the solid support to produce a solution phase mixture of first moieties. In this step of the subject methods, the array is subjected to cleavage conditions sufficient to cleave the immobilized first nucleic acids of the features from the substrate surface. Generally, this step comprises contacting the array with an effective amount of a cleavage agent. The cleavage agent will, necessarily, be chosen in view of the particular nature of the cleavable region of the cleavable domain that is to be cleaved, such that the region is labile with respect to the chosen cleavage agent. Where the cleavable domain comprises a photocleavable or photolabile group, cleavage can be effectuated by subjecting the cleavable domain to light of the appropriate wavelength sufficient to cleave the cleavable region.

Likewise, for chemically cleavable moieties, the array can be contacted with a chemical capable of cleaving the linker, e.g. the appropriate acid or base, depending on the nature of the chemically labile moiety. Suitable cleavable sites include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions) and diisopropyl-dialkoxysilyl (cleavable by fluoride ions). Other cleavable sites will be apparent to those skilled in the art or are described in the pertinent literature and texts (e.g., Brown (1997) Contemporary Organic Synthesis 4(3); 216-237).

Similarly, in those embodiments where the cleavable domain includes a restriction endonuclease recognized sequence, the array is contacted with an effective amount of the appropriate restriction endonuclease that recognizes and cleaves the sequence.

The above-described methods result in the production of a plurality of solution phase nucleic acids, where each of the different variable domains of the precursor array is represented in the plurality, i.e., for each feature present on the template array, there is at least one nucleic acid in the product plurality that corresponds to the feature, where by corresponds is meant that the nucleic acid is one that is generated by cleavage of a surface immobilized first nucleic acid of the feature of the array. The length of each of the product nucleic acids present in the resultant plurality ranges, in representative embodiments, from about 10 to about 1000 nt, such as from about 20 to about 500 nt, including from about 30 to about 120 nt.

The plurality of nucleic acids produced in these embodiments of the subject methods is characterized by having a known composition. By known composition is meant that, because of the way in which the plurality is produced, the sequence of each distinct nucleic acid in the product plurality can be predicted with a high degree of confidence. Accordingly, the sequence of each individual or distinct nucleic acid in the product plurality is known. In many embodiments, the relative amount or copy number of each distinct nucleic acid of differing sequence in the plurality is known. Put another way, the product plurality of nucleic acids is known to include a constituent nucleic acid corresponding to each feature of the precursor array used to produce it, such that each feature of the precursor array is represented in the product plurality.

In representative embodiments, the amount or copy number of each distinct nucleic acid of differing sequence in the product plurality is known. The amounts of each distinct nucleic acid in the product plurality may be equimolar or non-equimolar, and are conveniently chosen and controlled by employing a precursor array with the desired number of features (as well as molecules per/feature) for each member of the plurality. For example, where a product plurality that is equimolar for each member nucleic acid is desired, a precursor array with the same number of features for each member nucleic acid is employed. Alternatively, where a product plurality is desired in which there are twice as many nucleic acids of a first sequence as compared to a second sequence, a precursor array that has two times as many features of the first sequence as compared to the second sequence may be employed.

A feature of the nucleic acids of the product pluralities is that they are single-stranded ribonucleic acids. As such, the nucleic acids of the subject pluralities are not hybridized to complementary nucleic acids. In other words, the constituent nucleic acids of the product pluralities are not hybridized to separate nucleic acids of complementary sequence, where the separate nucleic acids are not covalently joined to them. While the product nucleic acids of the plurality are single-stranded, they may be linear or assume some secondary configuration, e.g., a hairpin configuration, and the like. The number of different or distinct nucleic acids present of differing sequence in the product plurality may vary, but is generally at least 2, at least 5, at least 10, such as at least about 20, at least about 50, at least about 100 or more, where the number may be as great as about 1000, about 5000 or about 25,000 or greater. Any two given nucleic acids in the product pluralities are considered distinct or different if they include a stretch of at least 20 nucleotides in length in which the sequence similarity is less then 98%, as determined using the FASTA program (using default settings).

The product plurality of nucleic acids may be a heterogeneous mixture or set of individual homogeneous nucleic acid compositions, depending on the intended use of the product plurality.

For those embodiments where the product plurality is a mixture, the term mixture refers to a heterogeneous composition of a plurality of different ribonucleic acids that differ from each other by residue sequence. Accordingly, the mixtures produced by the subject methods may be viewed as compositions of two or more nucleic acids that are not chemically combined with each other and are capable of being separated, e.g., by using an array of complementary surface immobilized nucleic acids, but are not in fact separated.

In those embodiments where the plurality of nucleic acids is a set of homogenous nucleic acid populations, the constituent members of the set are, in certain embodiments, physically separated, such as present on different locations of a solid support (e.g., of the precursor array), present in different containment structures, and the like.

The product pluralities of nucleic acids are physically separated from the precursor array as part of or following the cleavage step, as described above. As such, the product of the first step of the subject methods is a solution phase mixture of nucleic acids.

The second step of the subject methods is to contact the solution phase mixture of nucleic acids with one or more reactants, as desired or necessary, under conditions sufficient to produce the desired product mixture of second molecules, e.g., nucleic acids. In the broadest sense, the one or more reactants may be any single or combination of reactive agents that, in the presence of the solution phase first moiety, e.g., nucleic acid, result in the production of the desired product molecule, e.g., product nucleic acids.

In certain representative embodiments, the one or more reactants employed in this step include an enzymatic activity.

While the enzymatic activity may vary greatly, in representative embodiments the enzymatic activity is a polymerase activity, particularly a template dependent polymerase activity, such as an RNA or DNA polymerase. In these embodiments, one or more reactants may make up an enzymatic reaction system, particularly a template dependent polymerase reaction system, where the system may or may not be an amplification system, where the system may include one or more additional reagents, such as NTPs, dNTPs, primers, buffers, mono- or divalent cations, etc., as illustrated in greater detail below.

The particular conditions in which the solution phase first moieties are contacted with the one or more reactants will, of course, vary, depending on the particular reaction to be performed. Illustrative conditions are provided below in connection with a description of representative applications of the subject methods.

As mentioned earlier, the above provided discussion has been made primarily in terms of nucleic acid embodiments solely for ease of description. As such, embodiments in which the array is an array of other types of chemical moieties, such as polypeptides or other biopolymers, fall within the scope of the present invention, have been envisioned by the inventors at the time of filing the present application (the present description of such being sufficient to demonstrate such) and are readily practiced by those of skill in the art based on the above description.

The subject methods find use in a variety of different applications, representative applications of which are now reviewed in greater detail in the following section.

Utility

The subject methods of producing product second molecules using a precursor array of surface immobilized first moieties find use in a variety of different applications, and are particularly suited for use in applications where a plurality of distinct or different biopolymers, such as nucleic acids or proteins, are to be simultaneously subjected or contacted with the same one or more reactants to produce a product of diverse second molecules. In other words, the subject methods are particularly suited for use is in applications where a common reactant(s) is contacted at the same time with a plurality of distinct precursor molecules to produce a plurality of distinct product molecules. The representative applications described in greater detail below are conveniently characterized as nucleic acid or polypeptide applications, depending on whether the precursor array is an array of nucleic acids or an array of polypeptides.

Nucleic Acid Applications

In these representative applications, the precursor array that is employed is an array of nucleic acids, as illustrated above. While a variety of different types of nucleic acid applications can be practiced by the subject methods, of interest are those applications described in U.S. application Ser. No. 09/628,472; the disclosure of which is herein incorporated by reference, which applications are modified to employ the composition of cleaved, solution phase first nucleic acids produced by the subject methods as a template composition, in lieu of the array of surface immobilized nucleic acids described therein. The applications described in this publication are now reviewed in greater detail. When these applications are performed according to the present invention, the array surface immobilized precursor nucleic acids described therein are cleaved prior to production of the overhang comprising template nucleic acids, such that the template of the reaction is not in an "array" format but is in solution phase, as illustrated further below.

In these particular applications, following cleavage of the first nucleic acids from the precursor array to produce a solution phase composition of first nucleic acids (referred to below as a template composition), the resultant template composition is employed to generate mixtures of nucleic acids by a template dependent polymerase reaction, in which the solution phase composition of first nucleic acids is employed as the template. The mixture of product nucleic acids produced by these applications is characterized by having a known composition. As such, at least the sequence of each individual or distinct nucleic acids in the product mixture of differing sequences is known. In representative embodiments, the relative amount or copy number of each distinct nucleic acid of differing sequence in the product mixture is known.

In these applications, each nucleic acid present in the mixture at least includes a variable domain that serves to distinguish it from any other nucleic acids in the mixture, i.e., any other nucleic acid that does not have the identical sequence—any nucleic acid that is not its copy. The variable domain, $S_{ij}$, is a nucleic acid that hybridizes under stringent conditions to gene i at location j and is capable of serving as a primer in reverse transcription beginning at base j. The number of different variable domains, $S_{ij}$, present in the mixture may vary, but is generally at least about 10, usually at least about 20 and more usually at least about 50, where the number may be as great as 25,000 or greater. In many embodiments, the number of different variable domains present in the mixture ranges from about 1000 to 25,000, usually from about 4,200 to 8,400. In addition to the distinguishing variable domain, the constituent members of the mixture may all share one or more domains of common sequence, depending on the particular protocol employed to generate the mixture, as described in greater detail below.

In the subject methods, the first step is generally to provide the solution phase mixture of template nucleic acids, using the methods as described above. Each distinct nucleic acid of the mixture of solution phase first nucleic acids includes a constant domain and a complement variable domain. The complement variable domain of each distinct probe has a sequence that is the complement of a variable or distinguishing domain found in a constituent member of the mixture of nucleic acids that is produced by the subject methods as described above, where by complement is meant that the variable and complement variable sequences hybridize under stringent conditions, e.g., as described above.

Because of the nature of the subject methods, as described below, each distinct complement variable domain will be represented in the nucleic acid mixture produced using the solution of first nucleic acids as template, i.e., the complement of each distinct complement variable domain sequence will be found in the mixture of nucleic acids produced by the subject methods. For example, where a solution phase mixture of first nucleic acids, i.e., a template composition, has 10 different nucleic acids that differ by complement variable domain such that it has 10 different complement variable domains, i.e., $cV_{1-10}$, the nucleic acid mixture produced by the subject methods as described below will have 10 different or distinct nucleic acids, where each different nucleic acid sequence in the mixture includes a sequence that is the complement of one of $cV_{1-10}$, i.e., $V_{1-10}$.

As mentioned above, in addition to the unique complement variable domain, each nucleic acid present in the template composition includes a common or shared constant domain that is one side, e.g., 3', of the complement variable domain.

This constant domain may range in length from about 20 to about 50, such as from about 20 to about 45 and including from about 25 to about 40 nt. The constant domain typically comprises at least one of the following constant sub-domains: a functional domain; a recognition domain and a linker domain. In representative embodiments, each solution phase nucleic acid contains at least a recognition sub-domain, and optionally a functional domain and/or a linker domain. These constant sub-domains may be grouped together on the nucleic acid or separated so as to flank the variable domain of the probe. As such, in certain embodiments these sub-domains are generally arranged in the order of functional domain, recognition domain and linker domain going from the 5' to the 3' end of the nucleic acid sequence, such that the linker domain is at the 3' terminus. In yet other embodiments, one or more of the domains, e.g., the functional sub-domain, may be present on the 5' end of the variable domain.

The optional functional sub-domain is generally a sequence that imparts or contributes some function to a duplex nucleic acid in which it is present. Functional domains of interest include: polymerase promoter sites, e.g., T3 or T7 RNA polymerase promoter sites, sequences unique with respect to the intended target organism for the array experiment (i.e. unique priming sites) and the like. The length of this functional domain typically ranges from about 10 nt to about 40 nt, usually from about 20 nt to about 30 nt The recognition sequence of the constant domain is typically a sequence that, when present in duplex format, is recognized and cleaved by a restriction endonuclease. A large number of restriction endonucleases are known to those of skill in the art. Specific restriction endonuclease recognized sites of interest that may make up the subject recognition sequence include, but are not limited to: Hinc II and the like. Generally, the length of the recognition domain ranges from about 4 nt to about 8 nt, usually from about 5 nt to about 6 nt The linker sub-domain of the subject constant domains is optional. The linker domain may be any convenient sequence, including random sequence or a non-polynucleotide chemical linker (e.g. an ethylene glycol-based polyether oligomer), where the sole purpose of the linker domain is to project the other domains of the probe away from the substrate surface. Generally, the linker domain if present, has a length ranging from about 1 to about 20, including from about 1 to about 15, such as from about 1 to about 10, for example from about 5 to about 10 nt.

In representative embodiments, each nucleic acid of the template mixture employed in the subject methods is described by the following formula:

3'-X-R-F-cV-5' wherein:
X is the optional linking domain;
R is the recognition domain;
F is the functional domain; and
cV is the complement variable domain, i.e., the complement of the variable domain, $cS_{ij}$, of the nucleic acid produced by the subject methods to which it hybridizes under stringent conditions;
where each of these elements are as described above.

Following provision of the template composition by the subject methods, as described above, the next step is to contact the solution phase template composition with a universal primer under hybridization conditions sufficient to produce a template composition that includes a plurality of overhang comprising duplex nucleic acids, where the overhang is made up of the complement variable domain of each nucleic acid of the template composition. The universal primer is capable of hybridizing to the constant domain, or at least a portion thereof (e.g., at least that portion immediately 3' of the complement variable domain). The universal primer has a length that is sufficient to prime template driven primer extension, where the length of the universal primer generally ranges from about 10 to about 45 nt, such as from about 15 to about 35 nt and including from about 20 to about 30 nt. In representative embodiments, the universal primer is the complement of the recognition and/or functional sub-domains of the constant domain of each nucleic acid in the template composition. As such, in representative embodiments the universal primer that is employed has a sequence described by the formula:

5'-cR-cF-3' wherein:
cR is the complement of the recognition domain; and
cF is the complement of the functional domain.

As mentioned above, the template composition following contact with the universal primer, as described above, is made up of duplex molecules made up of a first nucleic acid having a constant and complement variable domain and a second nucleic acid which is the universal primer and is hybridized to the constant domain (or at least that portion of the constant domain that is 3' of the variable domain complement). As such, the solution phase composition produced by this step is a composition of overhang comprising duplex nucleic acids, typically DNA, molecules, where the overhang is made up of the complement variable domain of each nucleic acid in the template composition.

This composition of overhang comprising duplex nucleic acids is then subjected to template dependent polymerase mediated reaction conditions sufficient to produce the desired mixture of product nucleic acids. The specific reaction conditions to which the composition of overhang comprising duplex nucleic acids is subjected may vary depending on the particular protocol used and/or the specific nature of the nucleic acid mixture to be produced therefrom. Specific reaction conditions of interest include, but are not limited to: linear PCR (Polymerase Chain Reaction); strand displacement amplification; and in vitro transcription. Each of these specific reaction conditions is now reviewed in greater detail.

Where the overhang comprising duplex nucleic acid composition is subjected to linear PCR conditions, the composition is contacted in an aqueous reaction mixture with a source of DNA polymerase, dNTPs and any other desired or requisite reagents under conditions sufficient to produce linearly amplified amounts of nucleic acids, e.g., under thermal cycling conditions. As such, the polymerase employed in the subject methods is generally, though not necessarily (e.g., where new polymerase is added after each cycle) a thermostable polymerase. A variety of thermostable polymerases are known to those of skill in the art, where representative polymerases include, but are not limited to: Taq polymerase, Vent® polymerase, Pfu polymerase and the like. The amount of polymerase present in the reaction mixture may vary but is sufficient to provide for the requisite amount of polymerase activity, where the specific amount employed may be readily determined by those of skill in the art. Also present in the reaction mixture is a collection of the four dNTPs, i.e., dATP, dCTP, dGTP and dTTP. The dNTPs may be present in varying or equimolar amounts, where the amount of each dNTP typically ranges from about 10 µM to 10 mM, usually from about 100 µM to 300 µM. Other reagents that may be present in the reaction mixture include: monovalent cations (e.g. Na$^+$), divalent cations (e.g. Mg$^{++}$), buffers (e.g. Tris), surfactants (e.g. Triton X-100) and the like. In this linear PCR embodiment of the subject methods, the reaction mixture is subjected to thermal cycling conditions in which the temperature of the reaction mixture is cycled through an annealing, primer extension and dissociation temperatures in a manner that results in the production of linearly amplified amounts of nucleic acid for each different sequence probe on the template composition. In representative embodiments, the annealing temperature typically ranges from about 50° C. to 80° C., usually from about 60° C. to 75° C. and is maintained for period of time ranging from about 10 sec. to 10 min., usually from about 30 sec. to 2 min. The primer extension temperature typically ranges from about 55° C. to 75° C., usually from about 60° C. to 70° C. and is maintained for period of time ranging from about 30 sec. to 10 min., usually from about 1 min. to 5 min. The dissociation temperature typically ranges from about 80° C. to 99° C., usually from about 90° C. to 95° C. and is maintained for period of time ranging from about 1 sec. to 2 min., usually from about 30 sec. to 1 min.

In strand displacement amplification, the composition of overhang comprising duplex nucleic acids is employed as primed template in linear amplification variations of the exponential amplification protocols described in Walker et al., Nucleic Acids Res. (1992) 20:1691-1696 and Walker et al., Proc. Nat'l Acad. Sci. USA (1992) 89:392-396; as well as in U.S. Pat. No. 5,648,211; the disclosure of which is herein incorporated by reference. Briefly, isothermal linear amplification is achieved as follows. Following production of the composition of overhang comprising duplex nucleic acids, the composition is subjected to a cycle of strand nicking of the universal primer after sequence cR, typically by using a restriction endonuclease. Generally, the template strand or probe sequence is protected via an appropriately placed phosphorthioate linkage in the surface-bound template strand. Extension of the 3' end exposed by the nick is then allowed to proceed by using a DNA polymerase that lacks a 5'→3' exonuclease activity but possesses a strand displacement activity, e.g., Klenow fragment. Each cycle in this protocol releases a nucleic acid molecule which has the formula: 5'-cF-Sij-3'. (It is noted that, depending on the nature of the initial array, the polarity of the product molecule may be reversed, e.g., the molecule may have the formula 3'-cF-Sij-5'.) In certain variants of this method, nicking may be achieved by making R a half-site for a restriction endonuclease that exhibits single-strand cleavage activity, or by employing a nicking endonuclease, such as N.BstNBI, and the like.

In yet other embodiments, the subject composition of overhang comprising duplex nucleic acids is employed in an in vitro transcription method. In this embodiment, the template composition may be one that includes nucleic acid molecules of the following formula:

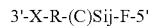

wherein:
X and R are as defined above;
F is an RNA polymerase promoter, e.g., T3 or T7 promoter; and
(C) Sij is Sij modified to end in a C residue.

The universal primer employed with this composition has the formula 5'-cR-3'. When the template composition is contacted with NTPs, T3 or T7 polymerase and the appropriate transcription buffer, ribonucleic acids of the formula: 5'-(rG)rcSij-rcF-3' are produced, where r stands for ribonucleotide. (It is noted that, depending on the nature of the initial array, the polarity of the product molecule may be reversed, e.g., the molecule may have the formula 3'-(rG)rcSij-rcF-5'.) By contacting this resultant mixture of ribonucleic acids with the DNA primer 5'-F-3' and a reverse transcriptase, a mixture of deoxyribonucleic acids suitable for use as primer in target generation protocols is produced.

The above described representative methods result in the production of a mixture of nucleic acids, typically a mixture of deoxyribonucleic acids, where each of the different complement variable domains of the template composition is represented in the mixture, i.e., there is at least one nucleic acid in the mixture that has a variable domain that hybridizes under stringent conditions to each different complement variable domain present on the template composition.

The nucleic acid mixtures produced in these representative applications find use in a variety of different applications, and are particularly suited for use as primers in the generation of target nucleic acids, e.g., for array based differential gene expression analysis applications. Where the subject nucleic acids mixtures are used as primers for target generation in gene expression analyses, the first step is to generate a population of target nucleic acids from an initial mRNA source or sample. By target nucleic acid is meant a nucleic acid that has a sequence, e.g., $S_{ij}$, which is either the same as, or complementary to, the sequence of an mRNA found in an initial sample, where the target may be DNA or RNA and be present in amplified amounts as compared to the initial amount of mRNA, depending on the particular target generation protocol that is employed.

In these embodiments, the target or image nucleic acids are produced from the subject nucleic acid mixtures generally through enzymatic generation protocols. Specifically, the target nucleic acids are typically produced using template dependent polymerization protocols and an initial mRNA source. The initial mRNA source may be present in a variety of different samples, where the sample will typically be derived from a physiological source. The physiological source may be derived from a variety of eukaryotic or prokaryotic sources, with physiological sources of interest including sources derived from single-celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of RNA to be analyzed from the physiological source from which it is derived, the physiological source may be subjected to a number of different processing steps, where such processing steps might include tissue homogenization, cell isolation and cytoplasm extraction, nucleic acid extraction and the like, where such processing steps are known to those of skill in the art. Methods of isolating RNA from cells, tissues, organs or whole organisms are known to those of skill in the art and are described in Maniatis et al. (1989), Molecular Cloning: A Laboratory Manual 2d Ed. (Cold Spring Harbor Press).

A number of different enzymatic protocols for generating image or target nucleic acids from an initial mRNA sample are known and continue to be developed. Any convenient protocol may be employed, where the particular protocol employed depends, at least in part, on a number of factors, including: whether one wants to generate amplified amounts of target or image nucleic acid; whether one wants to generate geometrically or linearly amplified amounts of target nucleic acid; whether bias in the amount of target can be tolerated, etc. A common feature of these representative applications is the use of the subject nucleic acid mixtures produced using the above described protocols as primer.

A number of nucleic acid amplification methods can be employed to generate the target nucleic acid from an initial mRNA source, where these methods can employ the subject nucleic acid mixtures as primer. Such methods include the "polymerase chain reaction" (PCR) as described in U.S. Pat. No. 4,683,195, the disclosure of which is herein incorporated by reference, and a number of transcription-based exponential amplification methods, such as those described in U.S. Pat. Nos. 5,130,238; 5,399,491; and 5,437,990; the disclosures of which are herein incorporated by reference. Each of these methods uses primer-dependent nucleic acid synthesis to generate a DNA or RNA product, which serves as a template for subsequent rounds of primer-dependent nucleic acid synthesis. Each process uses (at least) two primer sequences complementary to different strands of a desired nucleic acid sequence and results in an exponential increase in the number of copies of the target sequence.

Alternatively, amplification methods that utilize a single primer may be employed to generate target or image nucleic acids from an initial mRNA sample, where the subject nucleic acid mixtures are employed as primer. See e.g. U.S. Pat. Nos. 5,554,516; and 5,716,785; the disclosures of which are herein incorporated by reference. The methods reported in these patents utilize a single primer containing an RNA polymerase promoter sequence and a sequence complementary to the 3'-end of the desired nucleic acid target sequence(s) ("promoter-primer"). In both methods, the promoter-primer is added under conditions where it hybridizes to the target sequence(s) and is converted to a substrate for RNA polymerase. In both methods, the substrate intermediate is recognized by RNA polymerase, which produces multiple copies of RNA complementary to the target sequence(s) ("cRNA").

Whatever process is employed to generate the target nucleic acid, where representative protocols have been provided immediately above, the process may be modified to include the use of chemical analogs of nucleotides that have been modified to include a label moiety, e.g., an organic fluorophore, an isotopic label, a capture ligand, e.g., biotin, etc. As a result, the target nucleic acids produced using the subject nucleic acid mixtures as primers often are labeled, either directly or indirectly, for use in subsequent hybridization assays.

The above target generation protocols are merely representative and by no means inclusive of all of the different types of protocols in which the subject nucleic acid mixtures find use as primers.

The resultant populations of target nucleic acids find use as, inter alia, target in hybridization assays, such as gene expression analysis applications. Gene expression analysis protocols are well known to those of skill in the art, and the populations of target nucleic acids produced by the subject methods find use in many, if not all, of these protocols. In gene expression analysis protocols using the subject populations of labeled target, the population of labeled target is typically contacted with a population of probe nucleic acids, e.g., on an array, under hybridization conditions, usually stringent hybridization conditions. Following hybridization, non-bound target is removed or separated from the probe, e.g., by washing. Washing results in a pattern of hybridized target, which may be read using any convenient protocol, e.g., with a fluorescent scanner device. From this pattern, information regarding the mRNA expression profile in the initial mRNA sample from which the target population was produced may be readily derived or deduced.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. The data may be transmitted to the remote location for further evaluation and/or use. Any convenient telecommunications means may be employed for transmitting the data, e.g., facsimile, modem, internet, etc.

In addition to the above described representative applications in which template compositions of solution phase nucleic acids produced by the subject methods are used to generate mixtures of deoxyribonucleic acids, the methods of the present invention may also be used to generate template compositions of nucleic acids that are subsequently employed to generate pluralities of ribonucleic acids, as described in copending application Ser. No. 10/961,991 filed on Oct. 8, 2004.

In these representative applications, the subject methods are employed to produce a template composition of first nucleic acids, where each nucleic acid includes a RNA polymerase promoter domain and a variable domain. The variable domains of the features of the precursor array have sequences that are chosen based on the particular application in which the array is to be used, and specifically the intended use of the ribonucleic acid mixture produced using the array in accordance with the subject methods. The length of the variable domain may vary considerably and will be chosen based on the desired length of the resultant ribonucleic acids in the to be produced RNA composition within the synthesis constraints of the subject method. In representative embodiments, the length of the variable domain will range from about 10 to about 150 nt, such as from about 15 to about 100 nt and including from about 20 to about 80 nt.

Each of the nucleic acids of the template composition also includes an RNA polymerase promoter domain, which domain may be the same or different between or among the constituent members of the template composition. Suitable promoter domains or regions that find use in the subject methods are ones that are capable of initiating transcription of an operationally linked DNA sequence in the presence of ribonucleotides and an RNA polymerase under suitable conditions. The promoter domain or region is linked in an orientation to permit transcription of RNA, as described in greater detail below. The promoter region may include between about 15 and about 250 nucleotides, such as between about 17 and about 60 nucleotides, from a naturally occurring RNA polymerase promoter or a consensus promoter region, as described in Alberts et al. (1989) in Molecular Biology of the Cell, 2d Ed. (Garland Publishing, Inc.). Prokaryotic promoters or eukaryotic promoters may be employed, and in representative embodiments prokaryotic promoters are employed, such as phage or virus promoters. As used herein, the term "operably linked" refers to a functional linkage between the affecting sequence (typically a promoter) and the controlled sequence, e.g., the variable domain. The promoter regions that find use are regions where RNA polymerase binds tightly to the DNA and contain the start site and signal for RNA synthesis to begin. A wide variety of promoters are known and many are very well characterized. Representative promoter regions of interest include, but are not limited to: T7, T3 and SP6 as described in Chamberlin and Ryan, The Enzymes (ed. P. Boyer, Academic Press, New York) (1982) pp 87-108.

In these representative applications, the above-described template composition is then contacted with a RNA polymerase promoter complement composition under conditions sufficient to produce a composition of overhang containing duplex nucleic acids. The RNA polymerase promoter complement composition is a nucleic acid composition that is made up of one or more distinct types nucleic acids of different sequence, where a given nucleic acid member of the complement composition is capable of hybridizing to an RNA polymerase promoter domain present on a nucleic acid in the template composition. The complement composition may be homogeneous or heterogeneous, depending on whether there is a single RNA polymerase promoter domain represented in the template composition, or a plurality of different such promoter domains. The nucleic acid members of the complement composition have a length that is sufficient to bind to the complementary domain of the nucleic acids present in the template composition and produce a functional RNA polymerase promoter site, where the length of the constituent nucleic acid members may range from about 10 to about 45 nt, such as from about 15 to about 35 nt and including from about 20 to about 30 nt.

As mentioned above, the composition produced by this method is composition of duplex probe molecules made up of a first nucleic acid having a constant and complement variable domain and a second nucleic acid which is the universal primer and is hybridized to the constant domain (or at least that portion of the constant domain that is 3' of the variable domain complement). As such, the composition produced by this step is a composition of overhang comprising duplex nucleic acid, typically DNA, molecules, where the overhang is made up of the complement variable domain of each nucleic acid in the composition.

Optionally, the resultant composition of overhang comprising duplex surface immobilized nucleic acids or probes is then subjected to primer extension reaction conditions sufficient to produce a composition of full-length duplex nucleic acids. The specific primer extension reaction conditions to which the composition of overhang comprising duplex nucleic acids is subjected may vary, so long as the conditions produce the desired surface immobilized duplex nucleic acids. In representative embodiments, the composition is contacted in an aqueous reaction mixture with a source of DNA polymerase, dNTPs and any other desired or requisite primer extension reagents under conditions sufficient to produce the desired surface immobilized duplex nucleic acids.

Following production of the template composition, e.g., overhang or optional duplex template compositions, as described above, the resultant template composition is then subjected to in vitro transcription reaction conditions sufficient to produce the desired product ribonucleic acid plurality. During this step, the at least partially duplex DNAs produced in the first step of the methods are transcribed by RNA polymerase to yield RNA product. In this step, the at least partially duplex DNAs are contacted with the appropriate RNA polymerase in the presence of the four ribonucleotides, under conditions sufficient for RNA transcription to occur, where the particular polymerase employed will be chosen based on the promoter region present in the double-stranded DNA, e.g. T7 RNA polymerase, T3 or SP6 RNA polymerases, E. coli RNA polymerase, and the like. Suitable conditions for RNA transcription using RNA polymerases are known in the art, see e.g. Milligan and Uhlenbeck (1989), Methods in Enzymol. 180, 51.

Where desired, the RNA pluralities that are produced by the subject methods may be produced as labeled pluralities of RNAs. The label may be incorporated into the product RNAs using any convenient protocol, e.g., by employing labeled NTPs in the in vitro transcription reaction mixture, or by employing labeled RNA polymerase promoter complements.

These representative applications produce a plurality of ribonucleic acids, where each of the different variable domains of the template composition is represented in the plurality, i.e., for each nucleic acid present in the template composition, there is at least one ribonucleic acid in the plurality that corresponds to the feature, where by corresponds is meant that the nucleic acid is one that is generated by in vitro transcription using the variable domain of the feature as template. The length of each of the product ribonucleic acids present in the resultant plurality ranges, in representative embodiments, from about 10 to about 10000 nt, such as from about 100 to about 6000 nt, including from about 300 to about 2000 nt.

The product RNA pluralities of these representative applications find use in a variety of different applications, including, but not limited to: gene expression applications, e.g., as reference or control compositions, or in the estimation and/or correction of background; and gene-silencing applications, e.g., as RNAi agents. These applications are further described in copending application Ser. No. 10/961,991 filed on Oct. 8, 2004.

Polypeptide Applications

The subject methods of producing a population of product nucleic acid molecules from a precursor array of surface immobilized first moieties also find use in polypeptide applications. For example, an initial or precursor array having a plurality of distinct or different polypeptides immobilized on a surface of thereof may be subjected to cleavage conditions to produce a plurality of solution phase polypeptides, which composition may then be contacted with a conjugation reaction system that chemically bonds a common moiety of interest to each of the members of the solution phase composition to produce a plurality of second molecules, e.g., polypeptide conjugates.

Polypeptide precursor arrays of interest include, but are not limited to, arrays in which the polypeptide agents are chosen from affibodies, antigens, antigen-binding sites, antibodies, as well as binding fragments and mimetics thereof (e.g., fAB, scFV, etc.), receptors, ligands, protease targets, targets for kinases, etc. The polypeptide moieties may bind to a variety of different targets, including, but not limited to: affibodies, antigens, antigen-binding sites, antibodies, as well as binding fragments and mimetics thereof (e.g., fAB, scFV, etc.), receptors, ligands, protease targets, targets for kinases, as well as nucleic acid molecules, e.g., DNA, RNA including siRNAs, miRNAs, snRNAs, etc, aptamers, etc., and the like. In certain embodiments, the methods may further include a step of removing unbound polypeptides from the solution phase, following which the bound molecules may be detected by spectrally distinguishable labels, identifier tags included on a bound complex (which could be a label or biopolymer acting as a bar code for individual molecules), by immuniprecipitation, etc.

It is noted that the above reviewed nucleic acid and polypeptide applications are merely representative of the diverse types of applications in which the subject methods find use, and that the subject methods are not limited to use merely in the above representative applications.

Kits

Also provided by the subject invention are kits for use in practicing the subject methods. Generally, the kits include a precursor array, as described above, and a cleavage reagent. Depending on the particular application in which the kits are to be employed, the kits may further include additional containers, each with one or more of the various reagents (typically in concentrated form) utilized in specific applications, including, for example, buffers, dNTPs, polymerase, labeled dNTPs, etc.

A set of instructions will also typically be included, where the instructions may be associated with a package insert and/ or the packaging of the kit or the components thereof. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

What is claimed is:

1. A method comprising:
   (a) subjecting an array comprising a plurality of features, each comprising nucleic acids immobilized on a surface of a solid support via a cleavable domain having a cleavable region, to conditions sufficient to generate a solution phase composition of nucleic acids;
   (b) contacting said solution phase composition of nucleic acids with one or more reactants to produce a mixture of product nucleic acids; and
   (c) contacting said product nucleic acids with an addressable array of probe nucleic acids.

2. The method according to claim 1, wherein said cleavable region is recognized by a restriction endonuclease.

3. The method according to claim 1, wherein said one or more reactants comprises an enzymatic activity.

4. The method according to claim 3, wherein said one or more reactants make up a template dependent polymerase reaction system.

5. The method according to claim 4, wherein said template dependent polymerase reaction system is an amplification system.

6. The method according to claim 1, wherein said product nucleic acids are deoxyribonucleic acids.

7. The method according to claim 1, wherein said product nucleic acids are ribonucleic acids.

8. The method according to claim 1, wherein said method comprises cleaving said cleavable region prior to said contacting step.

9. The method according to claim 1, wherein said array comprising a plurality of features comprises surface immobilized single-stranded nucleic acids described by the formula:

surface-L-V wherein:
   L is a cleavable domain that includes a cleavable region; and
   V is a variable domain;
wherein only said variable domain V of said surface immobilized single-stranded nucleic acids differs between features.

* * * * *